(12) United States Patent
Cerboni et al.

(10) Patent No.: US 11,957,414 B2
(45) Date of Patent: Apr. 16, 2024

(54) INTRAOCULAR PRESSURE MEASURING AND/OR MONITORING DEVICE

(71) Applicant: SENSIMED AG, Etagnières (CH)

(72) Inventors: Sacha Cerboni, Vuarrens (CH); Mario Schlund, Ecublens (CH); Thierry Varidel, Fey (CH); Raphaël Fritschi, Lausanne (CH); Adrian Paraschiv, Geneva (CH)

(73) Assignee: SENSIMED AG, Etagnières (CH)

( * ) Notice: Subject to any disclaimer, the term of this patent is extended or adjusted under 35 U.S.C. 154(b) by 489 days.

(21) Appl. No.: 17/256,245

(22) PCT Filed: Jul. 6, 2018

(86) PCT No.: PCT/EP2018/068338
§ 371 (c)(1),
(2) Date: Dec. 28, 2020

(87) PCT Pub. No.: WO2020/007482
PCT Pub. Date: Jan. 9, 2020

(65) Prior Publication Data
US 2021/0204811 A1   Jul. 8, 2021

(51) Int. Cl.
*A61B 3/16* (2006.01)
*A61B 5/00* (2006.01)
(52) U.S. Cl.
CPC ............. *A61B 3/16* (2013.01); *A61B 5/0004* (2013.01); *A61B 5/6821* (2013.01);
(Continued)

(58) Field of Classification Search
None
See application file for complete search history.

(56) References Cited

U.S. PATENT DOCUMENTS 4,089,329 A * 5/1978 Couvillon, Jr. .......... A61B 3/16
128/903
4,628,938 A   12/1986 Lee
(Continued)

OTHER PUBLICATIONS

ISR and Written Opinion of PCT dated Apr. 26, 2019.

*Primary Examiner* — Jacqueline Cheng
*Assistant Examiner* — Samuel C Kim
(74) *Attorney, Agent, or Firm* — Thomas Coester Intellectual Property

(57) ABSTRACT

The present invention relates to an intraocular pressure measuring and/or monitoring device (1) comprising a contact lens (10) presenting an inner surface (101) and an outer surface (102), and a pressure sensor (2) united with said contact lens (10) and located such that it is applied against an eye (8) of a user for sensing the intraocular pressure (IOP) of said eye (8) when said contact lens (10) is worn by said user, characterized in that said contact lens (10) comprises a soft portion (11) and a rigid portion (12), said rigid portion (12) being adapted to at least partially rigidify a central portion of the inner surface (101) of said contact lens (10) so as to maintain said rigidified inner surface (101) with a curvature radius adapted to flatten at least a portion of the eye surface in contact with the pressure sensor (2) so as to reach a pressure equilibrium around the pressure sensor (2) when said contact lens (10) is worn by said user.

34 Claims, 5 Drawing Sheets

(52) U.S. Cl.
CPC .............. *A61B 2560/0214* (2013.01); *A61B 2562/0247* (2013.01); *A61B 2562/168* (2013.01)

(56) References Cited

U.S. PATENT DOCUMENTS

| | | | |
|---|---|---|---|
| 4,922,913 A | 5/1990 | Waters et al. | |
| 2002/0049374 A1* | 4/2002 | Abreu | A61B 5/4839 600/404 |
| 2002/0159031 A1* | 10/2002 | Kanngiesser | A61B 3/125 351/219 |
| 2009/0076367 A1* | 3/2009 | Sit | A61B 3/16 600/398 |
| 2013/0184554 A1 | 7/2013 | Elsheikh et al. | |
| 2014/0243645 A1* | 8/2014 | Leonardi | A61B 3/16 600/398 |
| 2015/0164321 A1* | 6/2015 | Weibel | A61B 3/16 600/405 |
| 2019/0274546 A1* | 9/2019 | Elsheikh | A61B 3/16 |

* cited by examiner

Tonometer

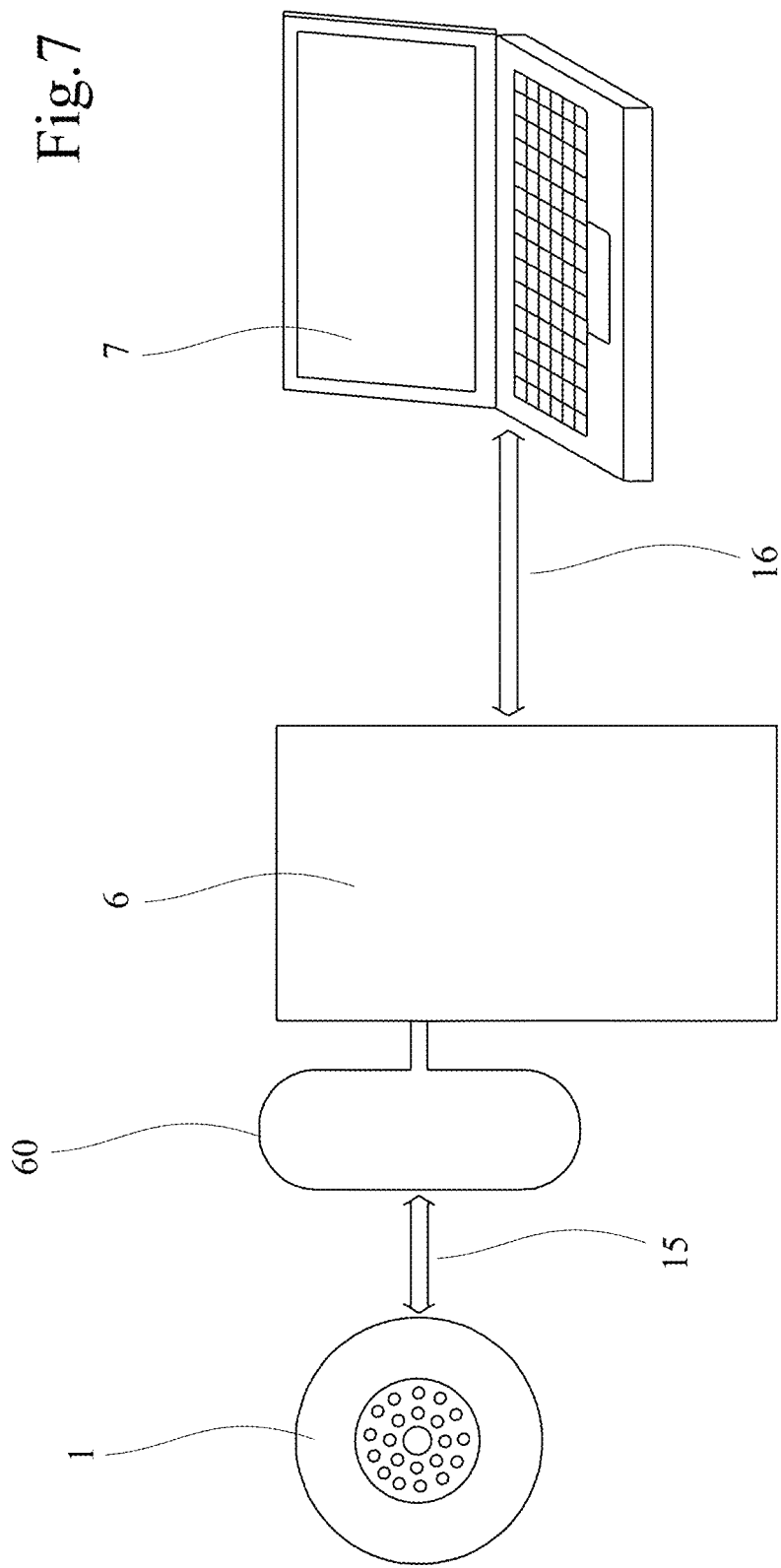

INTRAOCULAR PRESSURE MEASURING AND/OR MONITORING DEVICE

TECHNICAL FIELD

The present invention relates to a device for measuring and/or monitoring the intraocular pressure (IOP). The present invention relates in particular to a device that can be placed on the eye of a user to monitor intraocular pressure over an extended period of time, for example 8 hours, 12 hours, 24 hours or more.

BACKGROUND OF THE ART

Glaucoma is a widespread disease characterized by an elevated intraocular pressure (IOP). This elevated IOP produces a gradual loss of peripheral vision. There is therefore a need to have a detailed knowledge of IOP in glaucoma patients in order to provide reliable diagnostics or for setting up new therapies.

U.S. Pat. No. 4,922,913 describes an intraocular pressure sensor having a piezo-resistance strain gauge cell mounted in a curved holder which serves to position the planar pressure sensitive surface of the strain gauge cell against the surface of an eye. This sensor is specifically designed to be placed on the sclerotic portion of the eyeball (sclera), so that the pressure sensitive surface presses on the white part of the eye. The sensor is small, so that, when placed on the sclera, it is off-centered relative to the eye and it doesn't cover the cornea. The curved holder is made similarly to a hard contact lens.

A drawback of this intraocular pressure sensor is that it cannot be worn without interruption over extended periods of time because, like hard contact lenses, such a rigid holder rapidly provokes unbearable discomfort. Furthermore, the sensor is connected with wires to an external recording/monitoring apparatus, which is uncomfortable and requires that the recording/monitoring apparatus is kept relatively close to the user's head.

Another drawback of the pressure sensor of U.S. Pat. No. 4,922,913 is that a hard and small off-centered curved holder will significantly slide and move on the eyeball, thus resulting in uncontrolled changes of the measurements' conditions and thereby compromising the accuracy of the IOP measurement. In order to avoid significant displacements and to maintain it in good contact with the eyeball, the curved holder of U.S. Pat. No. 4,922,913 must be placed under the eyelid.

Yet another drawback of this intraocular pressure sensor is that the rigid holder must be manufactured or at least customized specifically for each user. A hard holder must indeed be perfectly adapted to the particular shape and size of the user's eyeball for it to properly fit and not disturb the user when worn. This individualization of the sensor thus increases its manufacturing costs.

An aim of the present invention is therefore to provide an intraocular pressure monitoring device that can be easily adapted to a large number of patients by minor modifications of its external shape and where different sizes can be considered for the same application in order to adapt to uncommon eye dimensions.

Another aim of the present invention is to provide an intraocular pressure monitoring device that is comfortable for the user to wear without interruption on extended periods of time such as 24 hours.

Also, a patent document EP11764227.2 describes a soft contact lens and a pressure sensor united with, for example embedded in, the soft contact lens, the pressure sensor being located such that it is applied against an eye of a user for sensing the intraocular pressure (IOP) of the eye when the soft contact lens is worn by the user, wherein the soft contact lens is softer than a surface of the eye and is configured to adapt its shape to the shape of the eye under the effect of a suction force generated by capillary force of the tear film under the contact lens and maintaining it on the eye when the user is wearing the contact lens.

Patent document US2002/0159031A1 describes a device, basically a tonometer, for measuring intraocular pressure comprising a pressure sensor embedded within a base body such as a contact lens which can be either soft or rigid. A particular feature of this device is that the device is in direct contact with the eye surface and that its contact surface has a radius of curvature which permits to eliminate any radial forces at the center of the cornea. However a problem of this device is that the contact intended to be obtained using a hard or soft contact lens is not delivering IOP output to a user because no indication on the data transmission is described for the contact lens application leaving completely unexplained the way the sensor output should be made available.

Further hard and/or semi-rigid contact lenses usually maintain their shape when placed on the cornea and/or on the sclera of a human eye. Therefore, if the shape of the hard contact lens is not perfectly adapted to the shape of the eyeball, it will locally deform and/or hurt the user's eye. Furthermore, the contact lens will easily slide over the eyeball's surface and/or pop out of the eye.

On the other hand, soft contact lenses are less rigid, or softer, than the cornea of a human eye. Therefore, when placed on the eyeball, the shape of the soft contact lens will adapt to the shape of the user's cornea, thereby minimizing disturbances for the user and maximizing the adherence of the contact lens to the eyeball under the effect of a suction force generated by capillary force of the tear film under the contact lens, however, the softness of the contact lens generally results in having the contact lens bended over time by both the capillary forces if fitting is not adapted to the eye of the user and eye dimensions variations. The absence of rigid element for mechanical insulation of the sensor will not allow IOP reading under the effect of radial deformation of the soft contact lens acting on the sensor.

In this regard, a primary object of the invention is to solve the above-mentioned problems and more particularly to provide a pressure sensitive device accurately measuring IOP over a large period of time while allowing data transmission wirelessly.

Another object of the invention is to provide a new contact lens-like pressure sensitive device providing the advantages of both the hard and soft contact lenses without their drawbacks.

SUMMARY OF THE INVENTION

The above problems are solved by the present invention.

A first aspect of the invention is an intraocular pressure measuring and/or monitoring device comprising a contact lens presenting an inner surface and an outer surface, and a pressure sensor united with the contact lens and located such that it is applied against an eye of a user for sensing the intraocular pressure of the eye when the contact lens is worn by the user, characterized in that the contact lens comprises a soft portion and a rigid portion, the rigid portion being adapted to at least partially rigidify the inner surface of the contact lens and maintain the curvature radius of the rigidified inner surface so as to flatten at least a portion of the eye surface in contact with the pressure sensor so as to reach a pressure equilibrium around the pressure sensor when the contact lens is worn by the user. Thanks to this one obtains a pressure sensitive device accurately measuring IOP over a large period of time since it is stable on the cornea surface while providing a favorable sensing area around the pressure sensor.

According to a preferred embodiment of the present invention, the contact lens is a soft contact lens and the rigid portion is a rigid insert. In this manner, the surface in contact with the eye is the soft contact lens and both pressure sensor and the rigid portion are encapsulated within that contact lens.

Preferably, the soft portion at least partially surrounds the rigid portion. Thus, allowing the contact lens to adapt to a variety of eye shape regardless of the corneal and scleral dimensions.

In a preferred manner, the rigid portion has a general shape similar to a meniscus lens. In this manner, it has the same general shape as the contact lens and more closely fits to the eye general shape.

Advantageously, the rigid portion is smaller in dimension compared to the soft portion and is centered in the contact lens. Thus, it can be more easily placed inside the contact lens since the center part of the contact lens is thicker.

Preferably, the rigid portion comprises a plurality of through holes. In this manner, it prevents hypoxia of the eye through the rigid insert and it also permits "riveting" the rigid insert within the contact lens.

According to a preferred embodiment of the present invention, the curvature radius of the rigidified inner surface is larger than the one of the outer surface. Thus, allowing the described adaptation of the device to a variety of eye dimensions.

Advantageously, it comprises a plurality of pressure sensors. In this manner, accuracy of the measurement can be improved through comparison of the results.

In a preferred manner, the soft portion material of the contact lens is configured so as to adapt its shape to the shape of the eye and to center the contact lens on the eye and stabilize the contact lens in the tangential sliding direction when the user is wearing the contact lens. Thus, comfort of use is improved.

Preferably, the soft portion of said contact lens is made of a material chosen in the group of hydrogels, silicone-hydrogels and silicones.

Advantageously, the rigid portion of said contact lens is made of a material chosen in the group of polymers, ceramics, glasses, metals, RGP and the like.

Alternatively, any one of the soft portion and the rigid portion of said contact lens is made of a material having a tunable stiffness or a stiffness gradient.

According to a preferred embodiment of the present invention, the contact lens further comprises a microprocessor for telemetry powering and data transfer. In this manner, this permits wireless transfer of data.

Preferably, the pressure sensor is a temperature compensated pressure sensor such that the effect of temperature on the value output of the pressure sensor is compensated by a specialized electronic circuit. Preferably, this consists in a separated component such as one or more resistors. Thus, accuracy of the measurement is enhanced.

Advantageously, the pressure sensor is in direct contact with the eye of the user when the user is wearing the contact lens. In this manner, a favorable contact is established between the pressure sensor and the measurement interface so as to improve the sensibility.

According to a preferred embodiment of the present invention, the pressure sensor is in indirect contact with the eye of the user when the user is wearing the contact lens. Thus, the pressure sensor is protected from the direct contact to the eye surface in order to improve comfort. Latter can then be in contact with a more suitable material.

In a preferred manner, the pressure sensor is located within a cavity formed in an inner concave side of the rigid insert, and wherein the cavity is filled with a pressure transparent filler material that covers the pressure sensor such that a layer of the filler material is located between the pressure sensor and the inner surface of the contact lens when the user is wearing the contact lens. In this manner, the pressure sensor is not in direct contact with the rigid insert.

Preferably, the filler material is a material softer than the rigid portion. Thus, allowing a perfect mechanical insulation of the pressure sensor.

According to a preferred embodiment of the present invention, the filler material is softer than the material of the soft portion. In this manner, radial forces transmitted by the soft material of the contact lens are without influence or attenuation on the pressure sensor.

In a preferred manner, the filler material is the same material as the material of the soft portion. In this manner, the device is more easily manufactured.

According to a preferred embodiment of the present invention, the cavity is formed in the center of the rigid portion. Thus, it is provided on the thicker portion of the contact lens.

Preferably, the inner surface of the contact lens beneath the cavity presents a softer surface than the rest of the inner surface beneath the rigid portion. In this manner, the IOP is transmitted with a lowered attenuation.

According to a preferred embodiment of the present invention, the inner surface of the contact lens beneath the cavity presents a surface softness similar than the rest of the inner surface beneath the rigid portion. Thus, achieving the mechanical insulation from the rigid insert without material discontinuity between the pressure sensor and the eye.

Advantageously, the rigidified inner surface of the contact lens is surrounded by contact lens edges made of soft material. Thus, the contact lens can easily be centered on the eye.

The pressure sensor can be an absolute pressure sensor or a relative pressure sensor.

According to a preferred embodiment of the present invention, it further comprises an annular groove provided on the inner surface of the contact lens under the rigidified inner surface of the contact lens. In this manner, a suction force is provided.

The capillary force that generates the suction force is given by the tension force at the liquid-air interface and by the pressure drop in the tear film. The major component on the capillary force is due to the pressure drop in the tear film and so the suction force can be approximated by:

$$F_{suction} \cong A_{tear\,film} * \Delta P_{tear\,film} \cong A_{tear\,film} * 2 * \gamma * \cos(\Theta)/t,$$

where $A_{tear\,film}$ is the area wetted by the tear film under the contact lens, $\gamma$ is the surface tension of the tear film, $\Theta$ is the contact angle between tear film and contact lens and $t$ is the thickness of the tear film.

A second aspect of the invention relates to a kit comprising an intraocular pressure measuring and/or monitoring device of the first aspect of the invention, and a portable recording device configured for communicating with the intraocular pressure measuring and/or monitoring device and for storing data received from the intraocular pressure measuring and/or monitoring device. The particular advantages of this kit of the invention being similar to the ones of the device of the first aspect of the invention, they will not be repeated here.

Preferably, the portable recording device is configured for powering the intraocular pressure measuring and/or monitoring device over a wireless inductive communication channel. Thus, this prevents the use of invasive wiring within the eye.

Alternatively, the contact lens comprises a miniaturized power source embedded within it.

A third aspect of the invention relates to an intraocular pressure monitoring system comprising an intraocular pressure measuring and/or monitoring device of the first aspect of the invention; a portable recording device configured for communicating with the pressure measuring and/or monitoring device and for storing data received from the intraocular pressure measuring and/or monitoring device; a computing device configured for communicating with the portable recording device for receiving and/or processing and/or storing data received from the portable recording device. The particular advantages of this system of the invention being similar to the ones of the device of the first aspect of the invention, they will not be repeated here.

Advantageously, the portable recording device is configured for powering the pressure measuring and/or monitoring device over a wireless inductive communication channel.

Preferably, the intraocular pressure monitoring system comprises two intraocular pressure measuring and/or monitoring device of the first aspect of the invention and the portable recording device is configured for communicating with the two intraocular pressure measuring and/or monitoring devices and for storing data received from the two intraocular pressure measuring and/or monitoring devices.

Furthermore, the intraocular pressure measuring and/or monitoring device of the invention doesn't need to be customized for each user, because it can be adapted to a large number of patients by having several sizes available that only differ in their external shape so as to easily adapt to different eye shapes and sizes. The intraocular pressure measuring and/or monitoring device can also be worn over a long period of time without discomfort for the user.

BRIEF DESCRIPTION OF THE DRAWINGS

Further particular advantages and features of the invention will become more apparent from the following non-limitative description of at least one embodiment of the invention which will refer to the accompanying drawings, wherein

FIG. 7 schematically represents an example of an intraocular pressure monitoring system of the present invention.

DETAILED DESCRIPTION OF THE INVENTION

The present detailed description is intended to illustrate the invention in a non-limitative manner since any feature of an embodiment may be combined with any other feature of a different embodiment in an advantageous manner.

Figure 1:
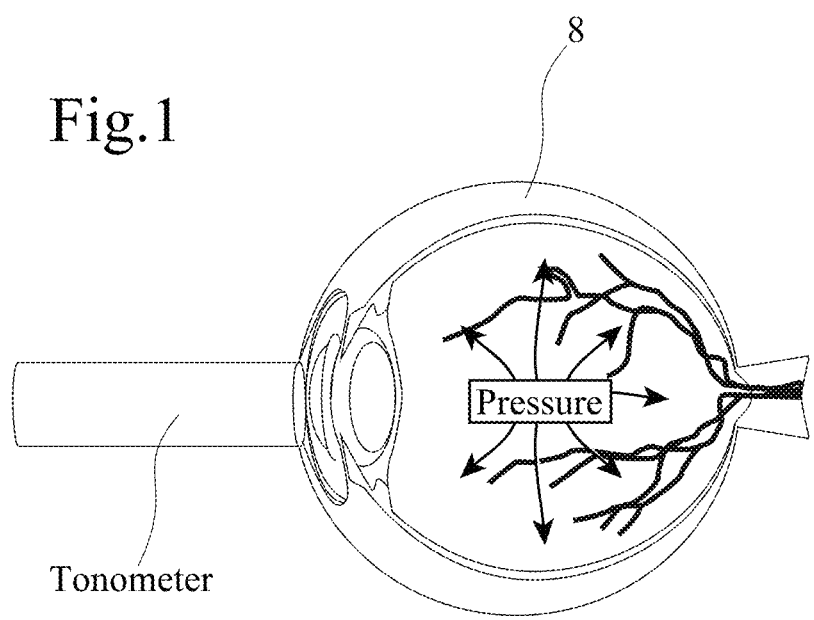
FIG. 1 represents the principle of a conventional tonometer.

FIG. 1 shows a conventional tonometer well known in the prior art comprising a force sensor applied against the cornea of an eye to sense the intraocular pressure of the eye 8. As explained above, a drawback of this device is its rigid and uncomfortable nature and that it can only provide a single discrete measurement and no overtime measurement.

Figure 2:
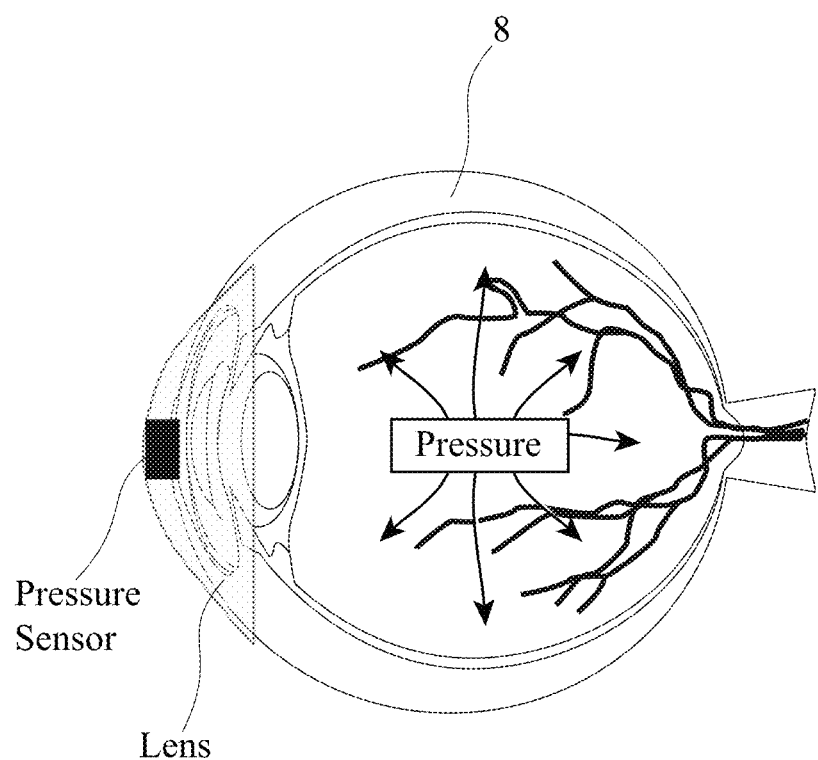
FIG. 2 represents the principle of a conventional contact lens comprising a pressure sensor.

FIG. 2 shows a conventional contact lens comprising a pressure sensor so as to act as a tonometer by putting the pressure sensor in contact with the cornea of the eye to detect the intraocular pressure of the eye. This figure is similar to the one of above mentioned prior art documents US2002/0159031A1 and EPI 1764227.2.

Figure 3:
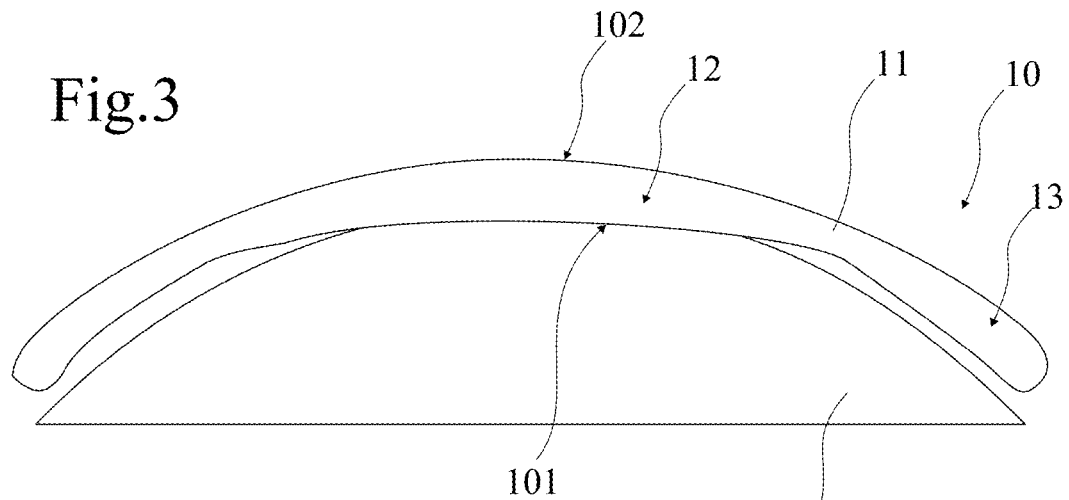
FIG. 3 schematically represents a first embodiment according to the present invention.

FIG. 3 shows a general and very schematic view of the contact lens 10 of the present invention including a rigidified central portion 12, a soft portion 11, edges 13 on an eye 8. It clearly appears that the radius of curvature of the inner rigidified surface is larger than the one of the eye so as to flatten the eye cornea upon use so as to reach a pressure equilibrium around the pressure sensor 2.

In FIG. 3, the rigid portion and the pressure sensor are not represented, such that one can clearly see the curvature radius of the rigidified inner surface 101 which is larger than the one of the outer surface 102 to influence the optical power of the lens. This figure also clearly illustrates the rigidified inner surface 101 of the contact lens 10 surrounded by contact lens edges 13 made of soft material which center and stabilize the contact lens.

Figure 4:
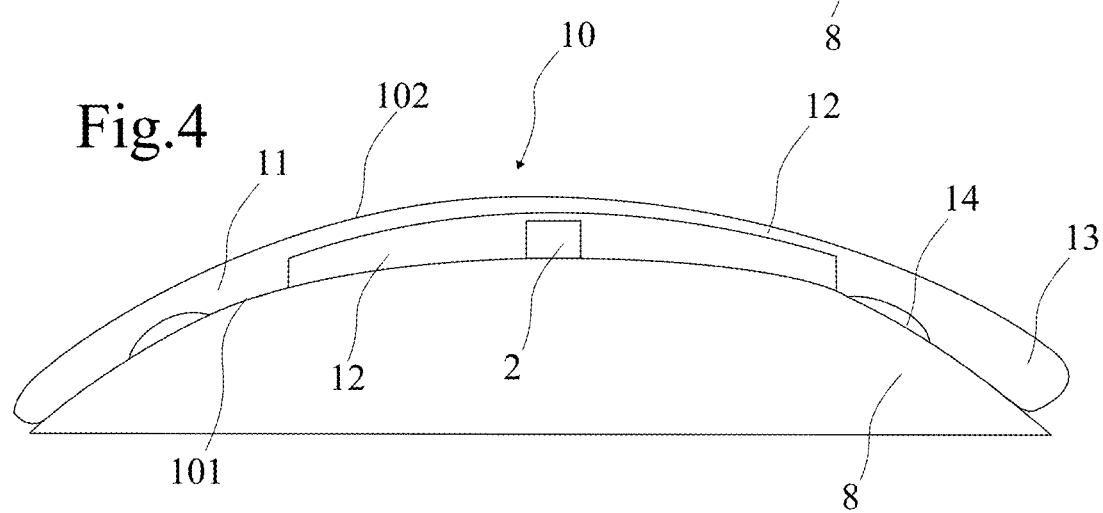
FIG. 4 represents the first embodiment according to the present invention more in detail.

FIG. 4 shows the intraocular pressure measuring and/or monitoring device 1 more in detail. According to the first embodiment of the invention it comprises a contact lens 10 such as a soft contact lens, presenting an inner surface 101 and an outer surface 102, and a pressure sensor 2 united with the contact lens 10 and located such that it is applied against an eye 8 of a user for sensing the intraocular pressure lop of the eye 8 when the contact lens 10 is worn by the user.

The contact lens 10 comprises a soft portion 11 and a rigid portion 12, the rigid portion 12, which is preferably a rigid insert as shown in FIG. 4, being adapted to at least partially rigidify the inner surface 101 of the contact lens 10 and provide the rigidified inner surface 101 with a curvature radius adapted to flatten at least a portion of the eye surface in contact with the pressure sensor 2 so as to reach a pressure equilibrium around the pressure sensor 2 when the contact lens 10 is worn by the user.

It also comprises an annular groove 14 provided on the inner surface 101 of the contact lens 10 just outside the rigidified inner surface of the contact lens 10.

The pressure sensor 2 is for example a miniaturized pressure sensor comprising a piezoresistive silicon micromachined pressure sensor on a ceramic, glass or silicon carrier. The pressure sensor 2 is either an absolute pressure sensor or a relative pressure sensor.

An advantage of using a relative pressure sensor in the pressure monitoring device of the invention is that, if the pressure around the back side of the diaphragm corresponds to the ambient or atmospheric pressure, the pressure measured by the pressure sensor essentially corresponds to the intraocular pressure (IOP), free from the effects of the ambient or atmospheric pressure that are due for example to changes in altitude and/or weather conditions.

An advantage of using an absolute pressure sensor, on the other hand, is that it is much easier to embed in the contact lens for manufacturing.

As shown, the soft portion 11 at least partially surrounds the rigid portion 12 which preferably has a generally meniscus or convex-concave lens shape and being smaller in dimension compared to the soft portion 11 and is centered in the contact lens. Preferably, the soft portion 11 material of the contact lens 10 is configured so as to adapt its shape to the shape of the eye 8 and center the contact lens 10 on the eye 8 and stabilize the contact lens in the tangential sliding direction when the user is wearing the contact lens 10.

Here it shall be understood that the term rigid portion 12 designates both the actual rigid insert embedded within the contact lens in order to rigidify a portion of the contact lens, but it can also designate a possible rigidified portion of the contact lens, preferably at the center of the lens, which is actually rigidified by the insert or the rigidified portion.

The preferred materials for the soft portion are any one chosen in the group comprising any preferably transparent soft materials such as group of hydrogels, silicone-hydrogels and silicones or any other soft material suitable for a contact lens.

On the other hand, the preferred materials for the rigid portion are any one chosen in the group comprising any preferably transparent materials such as polymers, ceramics, glasses, metals, RGP and the like that have a sufficient rigidity so to impose their shape to the cornea. This material can be shaped before being assembled (rigid insert) or be molded during the assembly process.

Alternatively, any one of the soft portion and the rigid portion of said contact lens is made of a material having a tunable stiffness or a stiffness gradient. An example of such material may comprise an elastomer composite embedded with phase-changing metal alloy or with shape memory polymer to reversibly tune the elastic rigidity of an elastomer composite. For example, it can be embedded with a sheet of low-melting-point Field's metal and an electric Joule heater composed of a serpentine channel of liquid-phase gallium-indium-tin (Galinstan®) alloy, for example. At room temperature, the embedded Field's metal is solid and the composite remains elastically rigid. Joule heating causes the Field's metal to melt and allows the surrounding elastomer to freely stretch and bend.

Another example comprises silicone elastomers with tunable stiffness. Herein, the capability to tune the stiffness of silicone materials is made via careful control over the chemistry, network formation, and crosslink density of the formulation.

In FIG. 4, the pressure sensor 2 is in direct contact with the eye of the user when the user is wearing the contact lens 10 in such case, the inner surface 101 of the contact lens 10.

Figure 5:
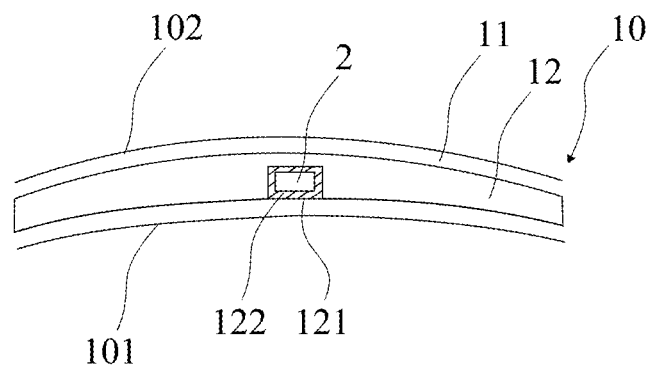
FIG. 5 schematically represents a second embodiment according to the present invention.

However, this is not necessarily the case, because as shown in FIG. 5, the pressure sensor 2 can be located within a cavity 121 formed in an inner concave side of the rigid portion 12, and the cavity 121 is filled with a pressure transparent filler material 122 that covers the pressure sensor 2 such that a layer of the filler material 122 is located between the pressure sensor 2 and the surface of the eye 8 when the user is wearing the contact lens 10. In this case, the pressure sensor 2 is in indirect contact with the eye of the user when the user is wearing the contact lens 10. The filler material 122 can be a material softer than the rigid portion 12 and also softer than the material of the soft portion 11. In this case, the inner surface 101 of the contact lens 10 beneath the cavity 121 presents a softer surface than the rest of the inner surface 101 beneath the rigid portion 12. Alternatively, the filler material 122 can be of the same softness as the material of the soft portion 11 and also can be the same material as the material of the soft portion 11.

Figure 6:
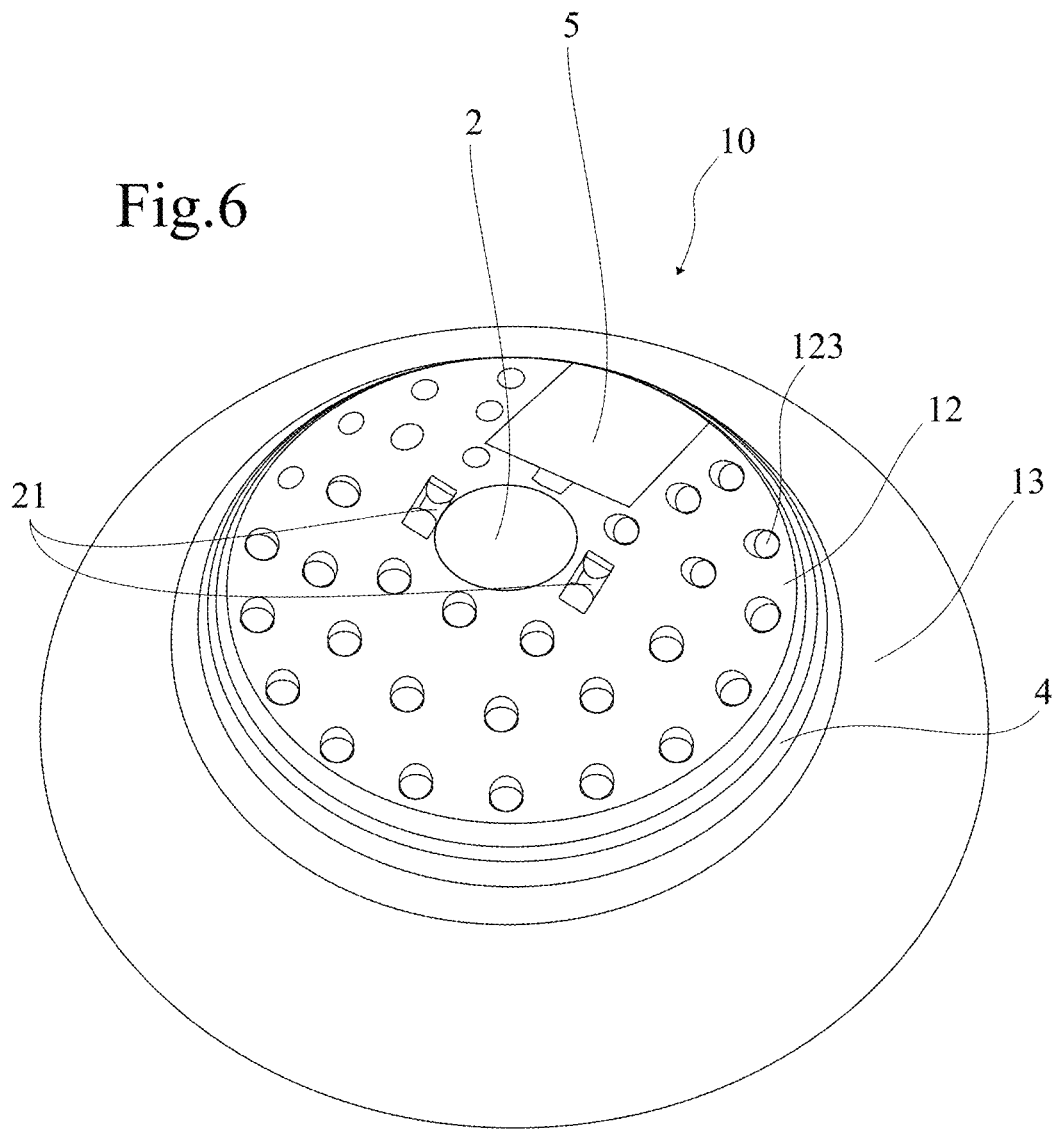
FIG. 6 schematically represents a third embodiment according to the present invention.

FIG. 6 shows a specific embodiment where the rigid portion 12 comprises a plurality of through holes 123. As shown in this figure, the contact lens 10 further comprises a microprocessor 5 and an antenna 4 for telemetry powering and data transfer between the contact lens and a processing unit.

In the embodiment illustrated in FIG. 6, the pressure sensor 2 is located in the center of the contact lens 10. According to this embodiment, the pressure sensor 2 is for example placed in a, for example circular, cavity formed in the center of the contact lens 10. Alternatively, the cavity 121 (not represented) is asymmetrical relative to the center of the contact lens 10, for example a round and off-centered cavity, a semi-annular groove or any other adapted shape. In this case, the microprocessor 5 is for example placed inside the contact lens 10.

Other cavity shapes and/or locations are however possible within the frame of the invention for placing the pressure sensor 2 and/or other elements of the pressure measuring and/or monitoring device 1 in the contact lens 10.

Also, in this figure, the pressure sensor 2 is a temperature compensated pressure sensor such that the effect of temperature on the value output of the pressure sensor is compensated by a specialized electronic circuit. In this example, this consists in a separated component such as one or more resistors which are to be located in the grooves 21. Of course, this is just an example and any other type of location of compensation circuit can be used.

Although not represented here, the device can comprise a plurality of pressure sensors 2 for accurate measurements.

According to the experimental data, inventors realized that temperature may modify the measured results; it is therefore preferable that the pressure sensor 2 is a temperature compensated pressure sensor such that the effect of temperature on the value output of the pressure sensor 2 is compensated by a specialized electronic circuit.

In a preferred embodiment, the intraocular pressure measuring and/or monitoring device 1, in particular the microprocessor 5 and/or the pressure sensor 2, is preferably wirelessly inductively powered through an antenna, for example by portable recording device 6. In a variant embodiment, the pressure measuring and/or monitoring device comprises a power source, for example a battery or micro fuel cell or a wireless energy source like infrared or solar cells, for powering the microprocessor 5 and/or the pressure sensor 2.

Another aspect of the invention is a kit comprising an intraocular pressure measuring and/or monitoring device 1 described above and a portable recording device 6 configured for communicating with the intraocular pressure measuring and/or monitoring device 1 and for storing data received from the intraocular pressure measuring and/or monitoring device 1. Preferably, the portable recording device 6 is configured for powering the intraocular pressure measuring and/or monitoring device 1 over a wireless inductive communication channel 15. If the kit comprises more than one pressure sensors, the portable recording device 6 is configured for communicating with all the intraocular pressure measuring and/or monitoring devices 1 and for storing data received from all the intraocular pressure measuring and/or monitoring devices 1.

Another aspect of the invention is an intraocular pressure monitoring system comprising an intraocular pressure measuring and/or monitoring device 1 described above; a portable recording device 6 configured for communicating with the pressure measuring and/or monitoring device 1 and for storing data received from the intraocular pressure measuring and/or monitoring device 1; a computing device 7 configured for communicating with the portable recording device 6 for receiving and/or processing and/or storing data received from the portable recording device 6.

FIG. 7 is a schematic representation of a typical intraocular pressure monitoring system using the intraocular pressure measuring and/or monitoring device 1 of the invention. According to the illustrated embodiment, the intraocular pressure monitoring system comprises the intraocular pressure measuring and/or monitoring device 1 of the present invention, a portable recording device 6 for communicating with the pressure measuring and/or monitoring device 1 and storing the collected information during the IOP monitoring periods, and a computing device 7, for example a personal computer, for storing, analyzing, computing and/or displaying the data collected and stored by the portable communication device 6.

The portable recording device 6 comprises a first communication interface for communicating with the pressure measuring and/or monitoring device 1. The first communication interface is for example a wireless communication interface comprising an antenna 60 that is advantageously placed near the contact lens when the pressure measuring and/or monitoring device 1 of the invention is worn by a user. The antenna 60 is for example integrated into eyeglasses, not represented on the figures, and/or into a for example disposable, flexible and hypoallergenic patch, also not represented on the figures, that are or is worn by the user during the IOP monitoring periods. Other means are however possible within the frame of the invention for placing the antenna 60 at a suitable distance from the pressure measuring and/or monitoring device 1 when the latter is worn by a user. The portable recording device 6 further comprises a second communication interface for communicating with the computing device 7.

When monitoring IOP, the user wears the pressure measuring and/or monitoring device 1 by placing the contact lens on his or her eye, just like any ordinary contact lens, and carries the portable recording device 6. The antenna 60 is placed as close as possible to the user's eye wearing the pressure measuring and/or monitoring device 1 in order to allow the establishment of a first wireless communication channel 15 between the pressure measuring and/or monitoring device 1 and the recording device 6. Preferably, the antenna 60 is furthermore oriented in a plane as parallel as possible to the plane of the antenna of the pressure measuring and/or monitoring device 1 of the invention in order to allow for an efficient powering of the microprocessor 5 and/or of the pressure sensor 2 over the communication channel 15, which is for example a close distance inductive communication channel 15. The antenna is for example integrated in eyeglasses and/or into a patch surrounding the eye, for example into a disposable, flexible and hypoallergenic patch, and/or in a cap or in another piece of clothing or accessory worn by the user. Preferably, the antenna 60 is centered with the antenna of the pressure measuring and/or monitoring device 1 when the pressure measuring and/or monitoring device 1 and the portable recording device 6 are both worn by the user. The diameter of the antenna 60 of the portable recording device 6 is preferably larger than the diameter of the pressure measuring and/or monitoring device 1. The shape of the antenna 60 of the portable recording device 6 is for example round, oval, rectangular, or any other appropriate shape. The shape of the antenna 60 of the portable recording device 6 is preferably adapted to the shape of the device, for example the eyeglasses, the patch, the piece of garment, etc., to which it is attached.

According to an embodiment, while monitoring IOP, the portable recording device 6 powers the pressure measuring and/or monitoring device 1 through the first communication channel 15 at for example regularly spaced time intervals and collects data sent by the microprocessor 5 through the antenna of the pressure measuring and/or monitoring device 1. Collected data for example comprises electrical resistance values of the gages of the pressure sensor 2 and/or a IOP value calculated by a microprocessor 5 of the pressure measuring and/or monitoring device 1. The collected data is stored in internal memory of the portable recording device 6. The intraocular pressure is for example measured at a frequency of 10 to 20 Hz during 10 to 60 seconds every 5 to 10 minutes. This allows a precise monitoring of the IOP variations over extended periods of time, including at night, while the user is asleep.

At some preferably predefined moments in time, for example once a day, once a week or once a month, the user and/or a practitioner connects the portable recording device 6 to a computing device 7, for example a personal computer, over a second, preferably wireless, communication channel 16, for example a Bluetooth communication channel. The second communication channel 16 can however also be a wired communication channel, for example a USB or any other appropriate communication channel. The data collected and stored in the internal memory of the portable recording device 6 is then transferred over the second communication channel 16 to the computing device 7 for further analysis and/or computing by the user and/or by the practitioner.

In variant embodiments, the intraocular pressure monitoring system comprises two pressure measuring and/or monitoring devices 1 in order to allow simultaneously monitoring both eyes of a patient, for example over extended periods of time. Preferably, both pressure measuring and/or monitoring devices 1 simultaneously and/or alternatively communicate with the same portable recording device 6 that for example is connected to and/or comprises two antennas. Accordingly, the portable recording device 6 preferably stores or records data received from both intraocular pressure measuring and/or monitoring devices 1.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This is for example particularly the case regarding the different apparatuses which can be used.

The invention claimed is:
1. Intraocular pressure measuring device (1) comprising:
 a contact lens (10) presenting an inner surface (101) and an outer surface (102), and
 a pressure sensor (2) united with said contact lens (10) and located such that the pressure sensor is applied directly against an eye (8) of a user for sensing the intraocular pressure (IOP) of said eye (8) when said contact lens (10) is worn by said user, characterized in that said contact lens (10) comprises a first portion (11) and a second portion (12), said second portion (12) being adapted to at least partially rigidify a central portion of the inner surface (101) of said contact lens (10) so as to maintain said rigidified inner surface (101) with a curvature radius adapted to flatten at least a portion of the eye surface in contact with the pressure sensor (2) so as to reach a pressure equilibrium around the pressure sensor (2) when said contact lens (10) is worn by said user.

2. The intraocular pressure measuring device according to claim 1, characterized in that the contact lens (10) is a soft contact lens and the second portion (12) is a rigid insert.

3. The intraocular pressure measuring device (1) according to claim 2, characterized in that said second portion (12) has a generally meniscus or convex-concave lens shape.

4. The intraocular pressure measuring device according to claim 1, characterized in that the first portion (11) at least partially surrounds the second portion (12).

5. The intraocular pressure measuring device (1) according to claim 4, characterized in that said second portion (12) is smaller in dimension compared to the first portion (11) and is centered in said contact lens.

6. The intraocular pressure measuring device (1) according to claim 1, characterized in that said second portion (12) comprises a plurality of through holes (123).

7. The intraocular pressure measuring device (1) according to claim 6, characterized in that said contact lens comprises soft material connections between the inner and outer surfaces through the through holes (123) of said second portion (12).

8. The intraocular pressure device according to claim 1, characterized in that the curvature radius of the rigidified inner surface (101) is larger than a curvature radius of the outer surface (102).

9. The intraocular pressure measuring device according to claim 1, characterized in that the pressure measuring device comprises a plurality of pressure sensors (2).

10. The intraocular pressure measuring device (1) according to claim 1, characterized in that a material of the first portion (11) of the contact lens (10) is configured so as to adapt a shape of the first portion to a shape of said eye (8) and center said contact lens (10) on said eye (8) and stabilize said contact lens in a tangential sliding direction when said user is wearing said contact lens (10).

11. The intraocular pressure measuring device (1) according to claim 1, characterized in that said first portion (11) of said contact lens (10) is made of a material chosen in the group of hydrogels, silicone-hydrogels and silicones.

12. The intraocular pressure measuring device (1) according to claim 1, characterized in that said second portion (12) of said contact lens (10) is made of a material chosen in the group of polymers, ceramics, glasses, metals, and rigid gas permeable lens materials.

13. The intraocular pressure measuring device (1) according to claim 1, characterized in that any one of the first portion (11) and the second portion (12) of said contact lens (10) is made of a material having a tunable stiffness or a stiffness gradient.

14. The intraocular pressure measuring device (1) according to claim 1, characterized in that said contact lens (10) further comprises an antenna (4) and a microprocessor (5) for telemetry powering and data transfer.

15. The intraocular pressure measuring device (1) according to claim 1, characterized in that the pressure sensor (2) is compensated in temperature such that the effect of temperature on the value output of the pressure sensor (2) is compensated by a specialized electronic circuit.

16. The intraocular pressure measuring device of claim 1 wherein both the first portion and the second portion are configured to directly contact the eye of the user when the contact lens is worn by the user.

17. An intraocular pressure measuring device (1) comprising:

a contact lens (10) presenting an inner surface (101) and an outer surface (102), and a pressure sensor (2) united with said contact lens (10) and located such that the pressure sensor is applied to sense the pressure of an eye (8) of a user through a pressure transmitting filler material for sensing the intraocular pressure (IOP) of said eye (8) when said contact lens (10) is worn by said user, characterized in that said contact lens (10) comprises a first portion (11) and a second portion (12), said second portion (12) being adapted to at least partially rigidify a central portion of the inner surface (101) of said contact lens (10) so as to maintain said rigidified inner surface (101) with a curvature radius adapted to flatten at least a portion of the eye surface in indirect contact with the pressure sensor (2) so as to reach a pressure equilibrium around the pressure sensor (2) when said contact lens (10) is worn by said user said pressure sensor (2) is in indirect contact with the eye of the user when said user is wearing said contact lens (10) and said pressure sensor (2) is located within a cavity (121) formed in an inner concave side of said second portion (12), and wherein said cavity (121) is filled with the pressure transmitting filler material (122) that covers said pressure sensor (2) such that a layer of said filler material (122) is located between said pressure sensor (2) and the inner surface of the contact lens (10).

18. The intraocular pressure measuring device (1) according to claim 17, characterized in that said filler material (122) is a material softer than the second portion (12).

19. The intraocular pressure measuring device (1) according to claim 17, characterized in that said filler material (122) is more rigid than a material of said first portion (11).

20. The intraocular pressure measuring device (1) according to claim 17, characterized in that said filler material (122) is softer than a material of said first portion (11).

21. The intraocular pressure measuring device (1) according to claim 17, wherein said filler material (122) is of the same softness as a material of said first portion (11).

22. The intraocular pressure measuring (1) according to claim 21, characterized in that said filler material (122) is a same material as the material of said first portion (11).

23. The intraocular pressure measuring device (1) according to claim 17, wherein said filler material (122) is a liquid.

24. The intraocular pressure measuring device (1) according to claim 17, characterized in that said cavity (121) is formed in a center of said second portion (12).

25. The intraocular pressure measuring device (1) according to claim 17, characterized in that a portion of said inner surface (101) of the contact lens (10) beneath said cavity (121) presents a softer surface than the rest of the inner surface (101) beneath the second portion (12).

26. The intraocular pressure measuring device (1) according to claim 17, characterized in that a portion of said inner surface (101) of the contact lens (10) beneath said cavity (121) presents a surface softness substantially the same as the rest of the inner surface (101) beneath the second portion (12).

27. The intraocular pressure measuring device (1) according to claim 1, characterized in that said rigidified inner surface (101) of the contact lens (10) is surrounded by contact lens edges (13) made of soft material.

28. The intraocular pressure measuring (1) according to claim 1, characterized in that the pressure measuring device further comprises an annular groove (14) provided on the inner surface (101) of the contact lens (10) under the rigidified inner surface of the contact lens (10).

29. Kit comprising:
an intraocular pressure measuring device (1) including: a contact lens (10) presenting an inner surface (101) and an outer surface (102), and
a pressure sensor (2) united with said contact lens (10) and located such that the pressure sensor can sense the interocular pressure (IOP) when the contact lens (10) is applied against an eye (8) of a user,
characterized in that said contact lens (10) comprises a first portion (11) and a second portion (12), said second portion (12) being adapted to at least partially rigidify a central portion of the inner surface (101) of said contact lens (10) so as to maintain said rigidified inner surface (101) with a curvature radius adapted to flatten at least a portion of the eye surface in contact with the pressure sensor (2) so as to reach a pressure equilibrium around the pressure sensor (2) when said contact lens (10) is worn by said user, wherein the pressure sensor (2) is nested in a recess in the second portion (12), the recess covered by the first portion; and
a portable recording device (6) configured for communicating with said intraocular pressure measuring device (1) and for storing data received from said intraocular pressure measuring device (1).

30. The kit according to claim 29, wherein said portable recording device (6) is configured for powering said intraocular pressure measuring device (1) over a wireless inductive communication channel (15).

31. The kit according to claim 29, further comprising a second intraocular pressure measuring device (1), wherein said portable recording device (6) is configured for communicating with said two intraocular pressure measuring devices (1) and for storing data received from said two intraocular pressure measuring devices (1).

32. Intraocular pressure monitoring system comprising:
an intraocular pressure measuring device (1) including: a contact lens (10) presenting an inner surface (101) and an outer surface (102), and
a pressure sensor (2) united with said contact lens (10) and located such that the pressure sensor is applied directly against an eye (8) of a user for sensing the intraocular pressure (IOP) of said eye (8) when said contact lens (10) is worn by said user,
characterized in that said contact lens (10) comprises a first portion (11) and a second portion (12), said second portion (12) being adapted to at least partially rigidify a central portion of the inner surface (101) of said contact lens (10) so as to maintain said rigidified inner surface (101) with a curvature radius adapted to flatten at least a portion of the eye surface in contact with the pressure sensor (2) so as to reach a pressure equilibrium around the pressure sensor (2) when said contact lens (10) is worn by said user;
a portable recording device (6) configured for communicating with said pressure measuring (1) and for storing data received from said intraocular pressure measuring and/or monitoring device (1); and
a computing device (7) configured for communicating with said portable recording device (6) for receiving and/or processing and/or storing data received from said portable recording device (6).

33. The intraocular pressure monitoring system according to claim 32, wherein said portable recording device (6) is configured for powering said pressure measuring (1) over a wireless inductive communication channel (15).

34. The intraocular pressure monitoring system according to claim 32 further comprising: a second intraocular pressure measuring (1), wherein said portable recording device (6) is configured for communicating with said two intraocular pressure measuring devices (1) and for storing data received from said two intraocular pressure measuring devices (1).

\* \* \* \* \*